US012810858B2

(12) United States Patent
Govari et al.

(10) Patent No.: US 12,810,858 B2
(45) Date of Patent: Nov. 24, 2026

(54) METHOD AND SYSTEM FOR VOICE ACTIVATED DISPLAY IN ELECTROPHYSIOLOGY PROCEDURES

(71) Applicant: BIOSENSE WEBSTER (ISRAEL) LTD., Yokneam (IL)

(72) Inventors: Assaf Govari, Haifa (IL); Vadim Gliner, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 143 days.

(21) Appl. No.: 18/612,280

(22) Filed: Mar. 21, 2024

(65) Prior Publication Data

US 2024/0386888 A1 Nov. 21, 2024

Related U.S. Application Data

(60) Provisional application No. 63/467,344, filed on May 18, 2023.

(51) Int. Cl.

| | |
|---|---|
| ***G10L 15/22*** | (2006.01) |
| ***G10L 15/08*** | (2006.01) |
| *A61B 17/00* | (2006.01) |

(52) U.S. Cl.

CPC ............ *G10L 15/22* (2013.01); *G10L 15/083* (2013.01); *A61B 2017/00203* (2013.01); *G10L 2015/088* (2013.01); *G10L 2015/223* (2013.01)

(58) Field of Classification Search

CPC ... G10L 15/22; G10L 2015/223; G10L 15/26; G10L 2015/088; G10L 15/00; G10L 15/083; G10L 2015/228; A61B 2017/00203; A61B 34/25; A61B 5/749

USPC .......................................................... 704/275

See application file for complete search history.

(56) References Cited

U.S. PATENT DOCUMENTS

| | | | |
|---|---|---|---|
| 5,391,199 | A | 2/1995 | Ben Haim |
| 5,443,489 | A | 8/1995 | Ben Haim |
| 5,558,091 | A | 9/1996 | Acker |
| 6,172,499 | B1 | 1/2001 | Ashe |
| 6,239,724 | B1 | 5/2001 | Doron |

(Continued)

FOREIGN PATENT DOCUMENTS

| | | | |
|---|---|---|---|
| EP | 2664293 | A1 | 11/2013 |
| WO | WO2017175232 | A1 | 10/2017 |

OTHER PUBLICATIONS

European Search Report for corresponding EPA No. 24176487.7 dated Jul. 5, 2024.

European Examination Report for 24176487.7 dated Oct. 22, 2025.

*Primary Examiner* — Vijay B Chawan

(74) *Attorney, Agent, or Firm* — Clayton, McKay & Bailey, PC

(57) ABSTRACT

A method, apparatus and computer program product, the method comprising: within an electrophysiology system executed by a computing platform and comprising a voice capture device: receiving an audio signal captured by an audio capture device; analyzing the audio signal to retrieve at least one trigger phrase; in response to identifying the trigger phrase, further analyzing the audio signal to identify one or more words associated with a user command; generating at least one code corresponding to the user command; and transmitting the at least one code to a driver of the computing platform, thereby causing execution of the user command by the electrophysiology system.

19 Claims, 5 Drawing Sheets

(56) References Cited

U.S. PATENT DOCUMENTS

| | | | | |
|---|---|---|---|---|
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben Haim | |
| 6,788,967 | B2 | 9/2004 | Ben Haim | |
| 6,892,091 | B1 | 5/2005 | Ben Haim | |
| 7,536,218 | B2 | 5/2009 | Govari | |
| 7,756,576 | B2 | 7/2010 | Levin | |
| 7,848,787 | B2 | 12/2010 | Osadchy | |
| 7,869,865 | B2 | 1/2011 | Govari | |
| 8,456,182 | B2 | 6/2013 | Bar-Tal | |
| 11,449,061 | B2 * | 9/2022 | Ebrahimi Afrouzi | A47L 11/4011 |
| 11,457,983 | B1 * | 10/2022 | Roh | A61B 34/25 |
| 2015/0187354 | A1 * | 7/2015 | Kim | G10L 15/22 704/246 |
| 2016/0217339 | A1 * | 7/2016 | Zhao | A61B 6/00 |
| 2017/0249940 | A1 * | 8/2017 | Chen | H04L 12/2829 |
| 2018/0322872 | A1 * | 11/2018 | Cha | G10L 15/22 |
| 2019/0278562 | A1 * | 9/2019 | Tang | G10L 15/02 |
| 2020/0152190 | A1 | 5/2020 | Itkowitz et al. | |
| 2020/0160856 | A1 * | 5/2020 | Kline | G06F 3/167 |
| 2020/0371744 | A1 * | 11/2020 | Liao | G06F 3/167 |
| 2021/0089040 | A1 * | 3/2021 | Ebrahimi Afrouzi | G05D 1/0248 |
| 2022/0066456 | A1 * | 3/2022 | Ebrahimi Afrouzi | G06F 3/04883 |
| 2024/0386888 | A1 * | 11/2024 | Govari | A61B 5/749 |

* cited by examiner

METHOD AND SYSTEM FOR VOICE ACTIVATED DISPLAY IN ELECTROPHYSIOLOGY PROCEDURES

CROSS-REFERENCE TO RELATED APPLICATIONS

The present application claims priority from U.S. Provisional Patent Application Ser. No. 63/467,344, filed May 18, 2023, entitled "METHOD AND SYSTEM FOR VOICE ACTIVATED DISPLAY IN ELECTROPHYSIOLOGY PROCEDURES" which is incorporated herein by reference.

FIELD OF THE DISCLOSURE

This disclosure relates generally to displaying information during an electrophysiology procedure, and specifically to a method for voice activation of the electrophysiology system.

BACKGROUND OF THE DISCLOSURE

Arrhythmias may be caused by problems with the electrical conduction system of the heart, and in particular electrical activity in one or more points or areas on a wall of a heart chamber.

In order to assess the status of the patient and decide on the treatment, such as applying one or more ablations, it may be required to assess the electrical activity at multiple locations on the heart wall. This activity may be obtained by a plurality of electrodes positioned on a distal tip of an intracardiac catheter inserted into one or more chambers of the heart.

Significant amounts of information may be displayed to a user, such as a physician performing the operation. The information may include but is not limited to an electro-anatomical model of a chamber of the heart, including for example a graphic representation of a plurality of signals obtained from the electrodes, information related to sites where ablation has been performed and the ablation parameters, and other types of information. In addition to manipulating the display, the electrophysiology system enables a user to perform a plurality of actions during the operation, such as marking locations, measuring distances, or the like.

BRIEF DESCRIPTION OF THE DRAWINGS

The present disclosure will be more fully understood from the following detailed description of the examples thereof, taken together with the drawings, in which.

DETAILED DESCRIPTION OF EXAMPLES

Figure 1A:
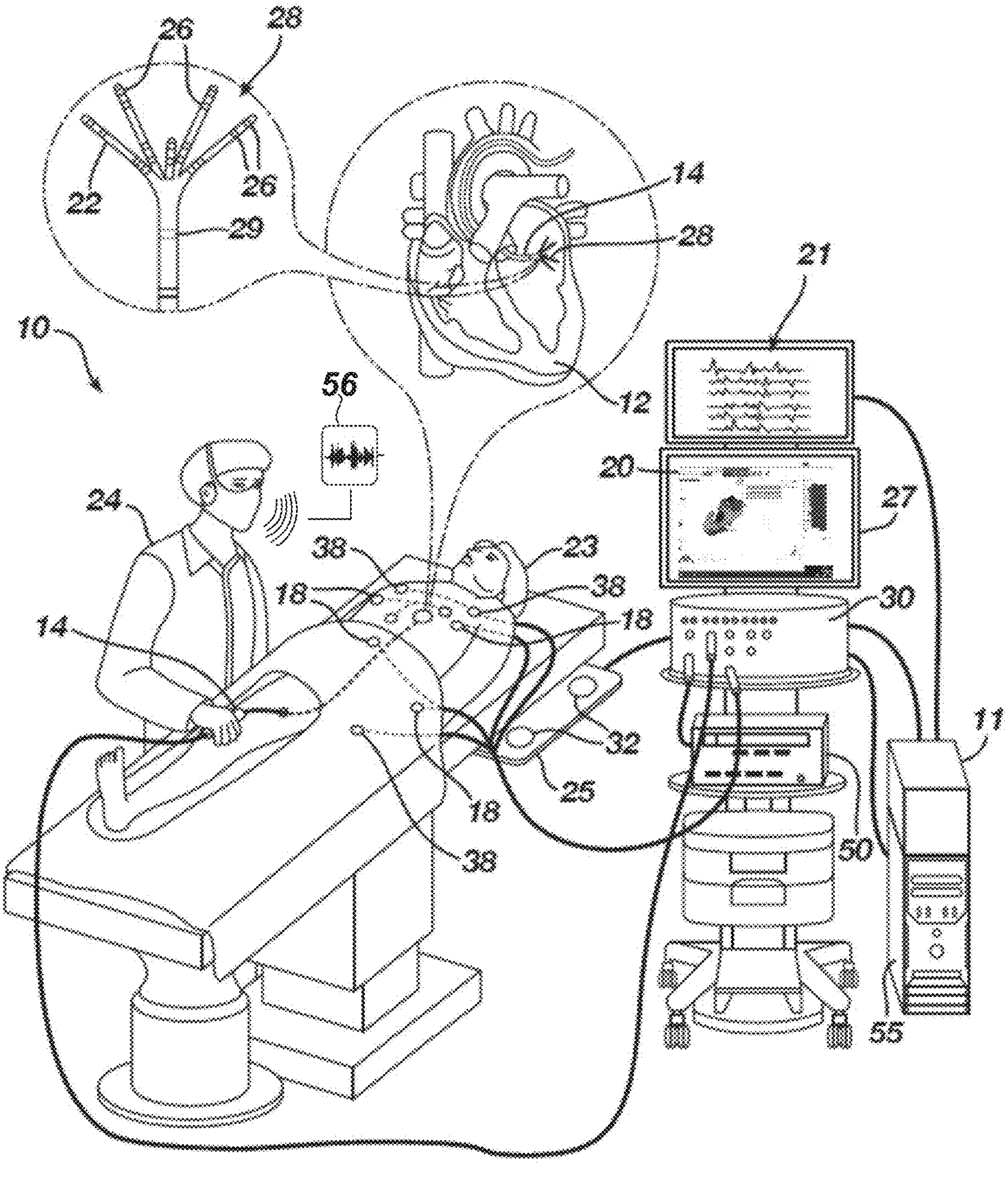
FIG. 1A is a schematic, pictorial illustration of a catheter-based electrophysiological (EP) mapping and ablation system, in accordance with some exemplary embodiments of the disclosure.

In the following description, numerous specific details are set forth in order to provide a thorough understanding of the present invention. It will be apparent to one skilled in the art, however, that the present invention may be practiced without these specific details. In other instances, well-known circuits, control logic, and the details of computer program instructions for conventional algorithms and processes have not been shown in detail in order not to obscure the present invention unnecessarily.

Software programming code, which embodies aspects of the present invention, is typically maintained in permanent storage, such as a computer readable medium. In a client-server environment, such software programming code may be stored on a client or a server. The software programming code may be embodied on any of a variety of known media for use with a data processing system. This includes, but is not limited to, magnetic and optical storage devices such as disk drives, magnetic tape, compact discs (CD's), digital video discs (DVD's), and computer instruction signals embodied in a transmission medium with or without a carrier wave upon which the signals are modulated. For example, the transmission medium may include a communications network, such as the Internet. In addition, while the invention may be embodied in computer software, the functions necessary to implement the invention may alternatively be embodied in part or in whole using hardware components such as application-specific integrated circuits or other hardware, or some combination of hardware components and software.

Overview

Arrhythmogenic tissue related to fibrillation may be identified by inspecting Intracardiac Electrogram (IEGM) at one or more locations along a heart wall, e.g., an inner wall, to detect the local potential caused by depolarization in each of the one or more locations. An IEGM thus records the heart's activity from within the heart, for example during a catheterization operation. IEGM is typically detected with one or more electrodes, e.g., one or more pairs of electrodes, mounted on a distal tip of an intracardiac catheter. In some example embodiments, the intracardiac catheter additionally includes a position sensor configured to track position of the distal tip.

Modern catheters have a plurality of electrodes distributed over a plurality of splines of the catheter, Where at any given time, each electrode samples the electrical activity at a location. For example, some catheters may have dozens or even a hundred or more electrodes.

It is appreciated that the plurality of electrodes enables the simultaneous collection of significant amount of data, and can give a good overall view of the electrical signals within the heart.

Additionally, other types of information may be available for display to a user such as a physician carrying out the operation, for example information about performed ablations and their parameters, and additional information items.

This abundance of information poses a challenge, as not all of it can always be displayed in a comfortable manner, due to the screen size and user attention limitations. Therefore, the user may need to switch between different views, for example display certain electrograms wherein the electrograms to be displayed may change over time, display characteristics of ablations performed at certain locations, or the like.

Changing the views or performing other activities may require navigating through options provided by a user interface (UI) of the system, opening menus, making selections in menus, typing keys which are translated to hotkeys, typing parameter values such as numbers of selected electrodes whose electrograms the user, e.g., the physician would like to inspect, or the like.

However, the user's hands are usually busy manipulating the catheter or other equipment, and are not free for adjusting the display or providing other commands to the system using an input device. Therefore, the user may ask the clinical assistants (CAS), having a computing platform operatively connected to the display viewable by the user, to adapt the display or perform the actions for the user. This arrangement, too, has significant disadvantages, such as the time delay until the view is updated, consisting of the time it takes the user to make the request plus the time it takes the CAS to perform it, and the additional burden on the CAS which occupies them and delays the performance of other required tasks.

In the disclosure below, the terms "command", "user command" or "user input command" are used interchangeably and relate to a feature or behavior of the electrophysiology system which a user can activate using a series of one or more keyboard and/or mouse and/or another pointing device inputs, hotkeys, shortcuts, or the like.

In accordance with some embodiments of the disclosure, the commands may be activated by receiving vocal commands from a user and translating them into a series of keyboard and pointing device inputs.

It is appreciated that a user of a system such as the electrophysiological system may need to remember and use the keyboard and/or pointing device actions in order to operate the corresponding user commands. Since such systems may comprise hundreds of user commands, it is appreciated that a user can only remember and use a fraction thereof.

Thus, in accordance with some exemplary embodiments, the user's voice may be received by a microphone associated with the computing platform executing the electrophysiological system. The microphone may be built-in into the computing platform, or an external microphone connected to the computing platform through a wired or wireless connection. An application or device comprising audio analysis capabilities may be installed on a computing platform executing the electrophysiological system, or operatively connected thereto, to receive and analyze the captured user's voice. The analyzed speech, comprising one or more words, may then be recognized to identify one or more user commands enabled for vocal activation. Each such user command may be translated into a series of one or more codes equivalent to the codes that may be generated when the user hits the keyboard or performs pointing device actions for executing the user command. The codes may be transmitted to the operating system driver, which in turn generates events such as keyboard or pointing device events that are appended or injected into the event queue (or message queue) of the underlying operating system, thereby triggering the required action. Thus, the audio spoken by the user initiates execution of the user command as if the user executed the series of keyboard or pointing device activities corresponding to the command.

In some embodiments, the words to be pronounced in order to activate a user command may be indicative of the user command, such as "display electrode number" followed by a number, in order to view the corresponding electrogram, "mark location" in order to mark a current location of the catheter, or the like.

In some embodiments, in order to reduce confusion, voice activation may be enabled for only a subset of the available user commands, for example the most frequently used ones. Confusion may be caused by the user saying a wrong command that is similar to the command the user intended, or by the misinterpretation of the words recognized in the audio, thereby executing a wrong user command. Thus, in some examples, at most about 50%, about 40%, about 25% or about 10% of the available user commands may be enabled via voice activation, such that the user can memorize and use them easily.

Some often used commands may include displaying certain data items, for example only electrograms obtained by certain electrodes and not by others, electrograms obtained only by bipolar electrodes and not by others, one or more tags showing ablation sites, information of a certain ablation site, or the like.

In some embodiments, only user commands comprising words from a limited lexicon may be identified, for example by using small vocabulary speech recognition. In additional embodiments, user commands may also be provided vocally as free text which may be recognized to determine the closest user command enabled for voice activation.

In some embodiments, the application may also comprise screen capture and image analysis modules to extract information presented on the screen. The captured screen may be analyzed for determining parameters of the system, such as types of catheter used, ablation locations or the like. Such information may be useful in determining the user commands for which voice activation is to be enabled. For example, if a catheter is used which comprises ten electrodes, a user can only ask to view an electrogram obtained by any of the ten electrodes, and a user command for showing electrogram no. 11 will not be enabled.

By adding a voice activation mechanism to activate commands and in particular frequently used commands, a user including the physician and/or the CAS, may manipulate the system more efficiently, without having to use their hands and without having to remember a plurality of action sequences, navigate through menus, or the like.

Moreover, the voice activation is provided externally to the electrophysiology system, and thus enables retrofitting of existing systems. Employing voice activation in accordance with the disclosure does not require any additional certification, testing, version update, or the like. All the options and user commands enabled by the electrophysiological system remain active and unchanged, but in addition some are also enabled via voice activation.

Capturing the user's voice and operating the user commands provided as vocal commands may continue throughout the operation, and in parallel to any other electrophysiological and display activity of the system. Thus, the user can always view the required data items, while keeping the user's hands free.

System Description

Reference is made to FIG. 1A showing an exemplary catheter-based electrophysiology mapping and ablation system 10. System 10 may include multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, one or more catheters may be inserted into the delivery sheath catheter so as to arrive at the desired location in heart 12. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. However, it is appreciated that the disclosure is equally applicable to any other type of catheter.

Physician 24 may place a distal tip 28 of catheter 14 in contact with the heart wall for sensing a target site in heart 12. For ablation, physician 24 may similarly place a distal end of an ablation catheter in contact with a target site for ablating tissue.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 may include one or more electrode patches 38 positioned for skin contact on patient 23 to establish location reference for location pad 25 as well as impedance-based tracking of electrodes 26. For impedance-based tracking, electrical current is directed to electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 may record multiple electrograms captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes 26 at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 may be an interface configured to establish electrical communication between catheters, other electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 may include memory, processor unit with memory or storage with appropriate operating software stored therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 or display device 21 activation sequences (or other data) compiled from recorded electrograms in representative visual indicia or imagery superimposed on the rendered anatomical map 20, optionally in accordance with user commands provided using user a interface or voice activation (3) displaying real-time location and orientation of multiple catheters within the heart chamber, and (4) displaying on display device 27 sites of interest such as places where ablation energy has been applied. One commercial product embodying elements of system 10 is available as the CARTO™ 3 System, available from Biosense Webster, Inc., 31A Technology Drive, Irvine, CA 92618.

The system may comprise a microphone for capturing speech by physician 24. The microphone may be embedded within workstation 55. Additionally or alternatively, the microphone may be external to workstation 55, and may be connected thereto via wired or wireless connection. An external microphone may be head mounted on the head of physician 24, fixed within the room, or located anywhere else within the system or its environment.

Workstation 55 or another computing platform as detailed below may further include modules for analyzing the audio captured from physician 24, retrieving user commands and displaying information on display devices 27 or 21 or performing other actions according to the user commands.

Figure 1B:
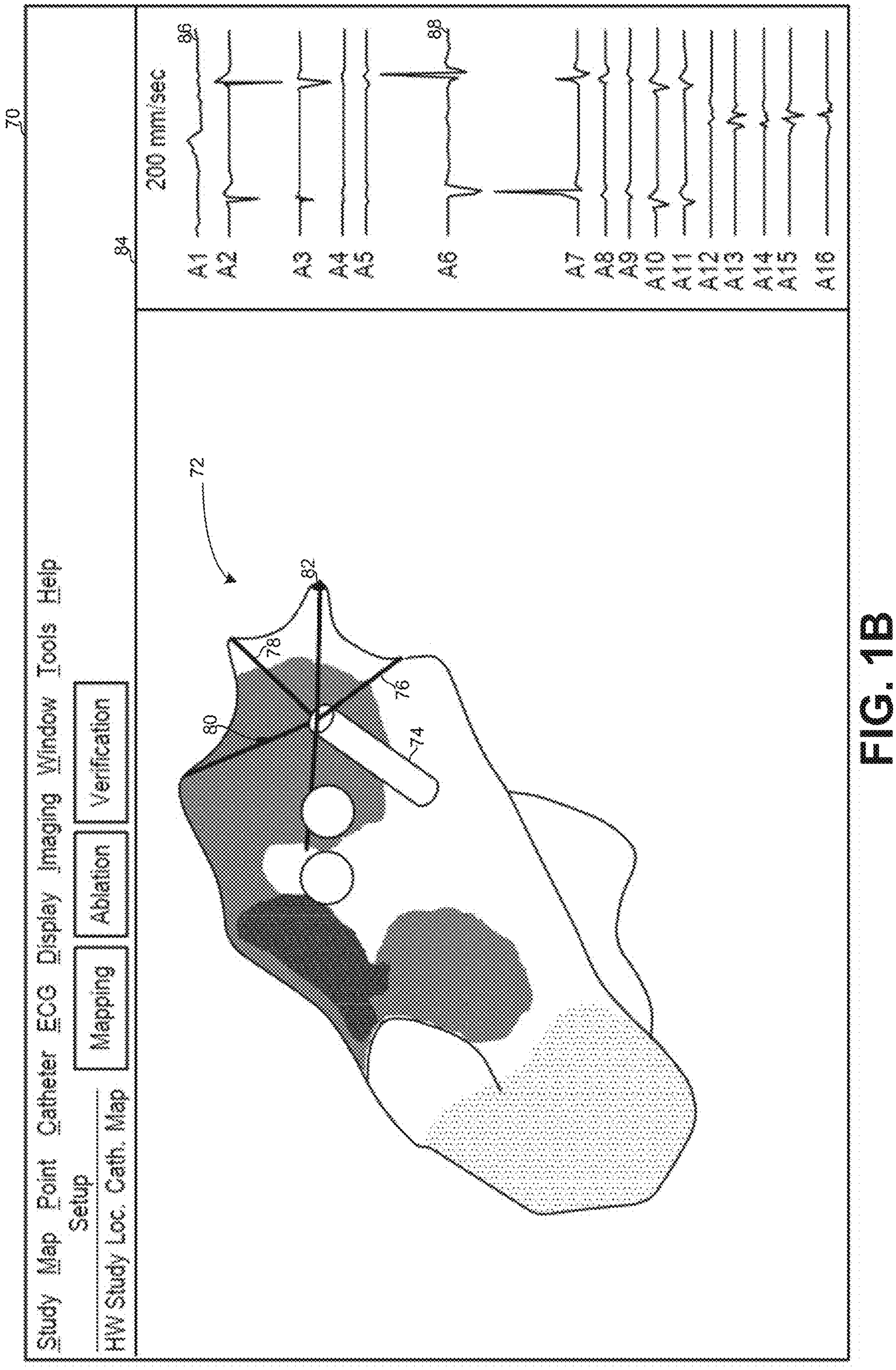
FIG. 1B is an enlarged schematic illustration of the display shown in FIG. 1A, in accordance with some exemplary embodiments of the disclosure.

Referring now to FIG. 1B, showing an enlarged schematic illustration of the display shown on display device 27 of FIG. 1A, in accordance with some exemplary embodiments of the disclosure.

The illustration, generally referred 70, shows a map 72 of the heart, color coded according to some parameter, such as the latency of their electrical activation. Map 70 also shows catheter 74 having a plurality of splines such as splines 76 and 78, each carrying one or more electrodes such as electrodes 80 and 82.

Illustration 70 further comprises right hand side pane 84, showing a plurality of electrograms such as electrograms 86 and 88, each originating from a different electrode of catheter 74.

Figure 1C:
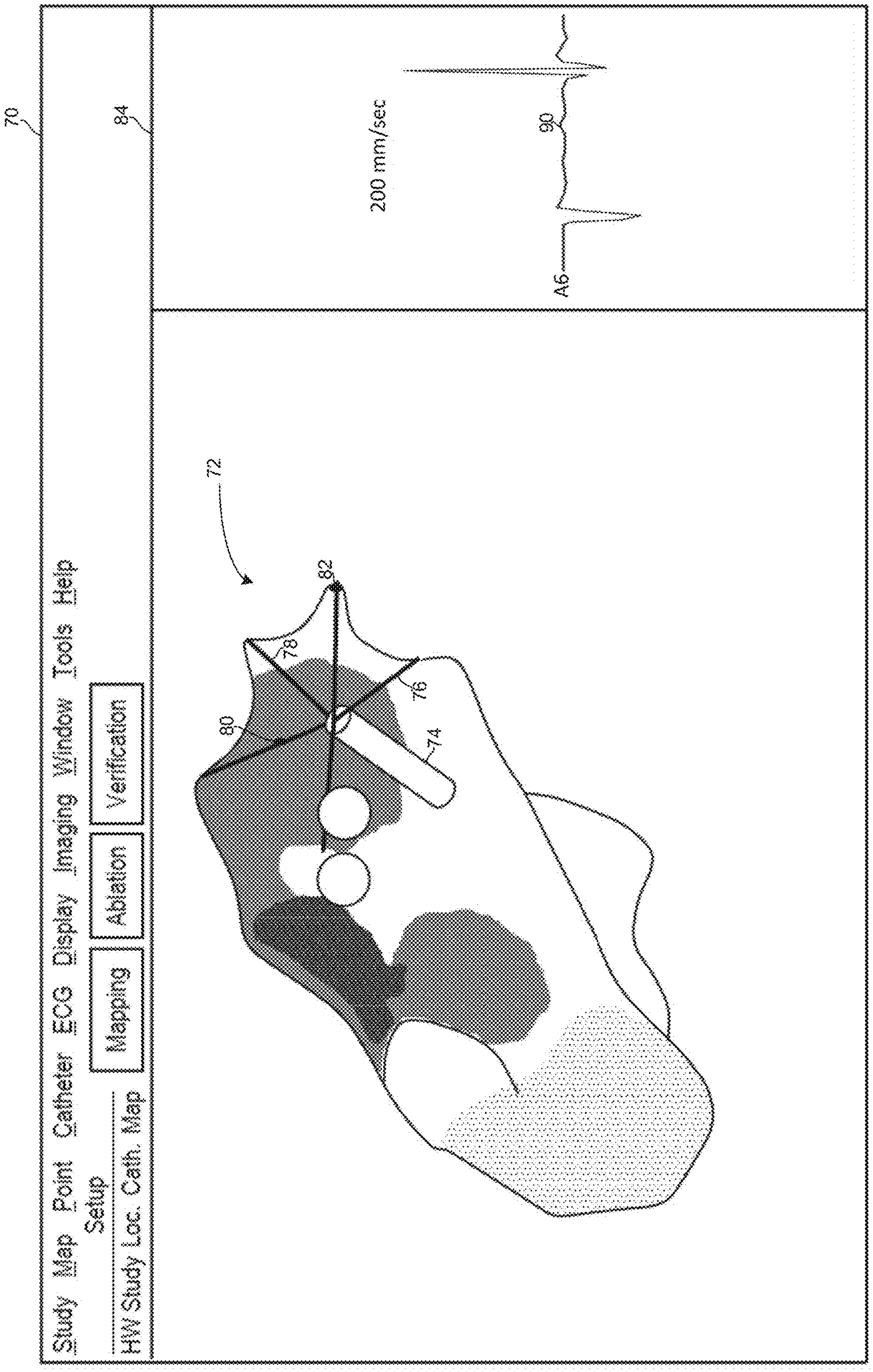
FIG. 1C is an enlarged schematic illustration of the display shown in FIG. 1A, subsequent to receiving and performing a vocal command from a user, in accordance with some exemplary embodiments of the disclosure.

Referring now to FIG. 1C showing an enlarged schematic illustration of the display shown on display device 27, subsequent to receiving audio comprising a user command from a user and executing it, in accordance with some exemplary embodiments of the disclosure.

The user command indicated that the user wishes to see only the electrogram obtained by electrode A6, such that the user can view it clearly without being disturbed by the plurality of electrograms. The user can make the system display only this electrogram by selecting a series of menu selections, typing electrode number or the like. In a system in accordance with the disclosure, the user may also issue a voice command that may achieve the same effect without the user having to remember the sequence of actions and while keeping the user's hands free.

Thus, while map 72 is the as in FIG. 1B, right hand side pane 84 shows only a single electrogram 90 as provided by electrode A6.

It is appreciated that a single electrogram as displayed in FIG. 1C is merely an example, and multiple other user commands may be issued vocally and activated, such as showing one or more electrograms over a shorter period of time, showing only electrograms positioned on a specific spline, rotating heart map 70 in a predetermined direction and angle, rotating heart map 70 in a required direction and angle, or the like.

Figure 2:
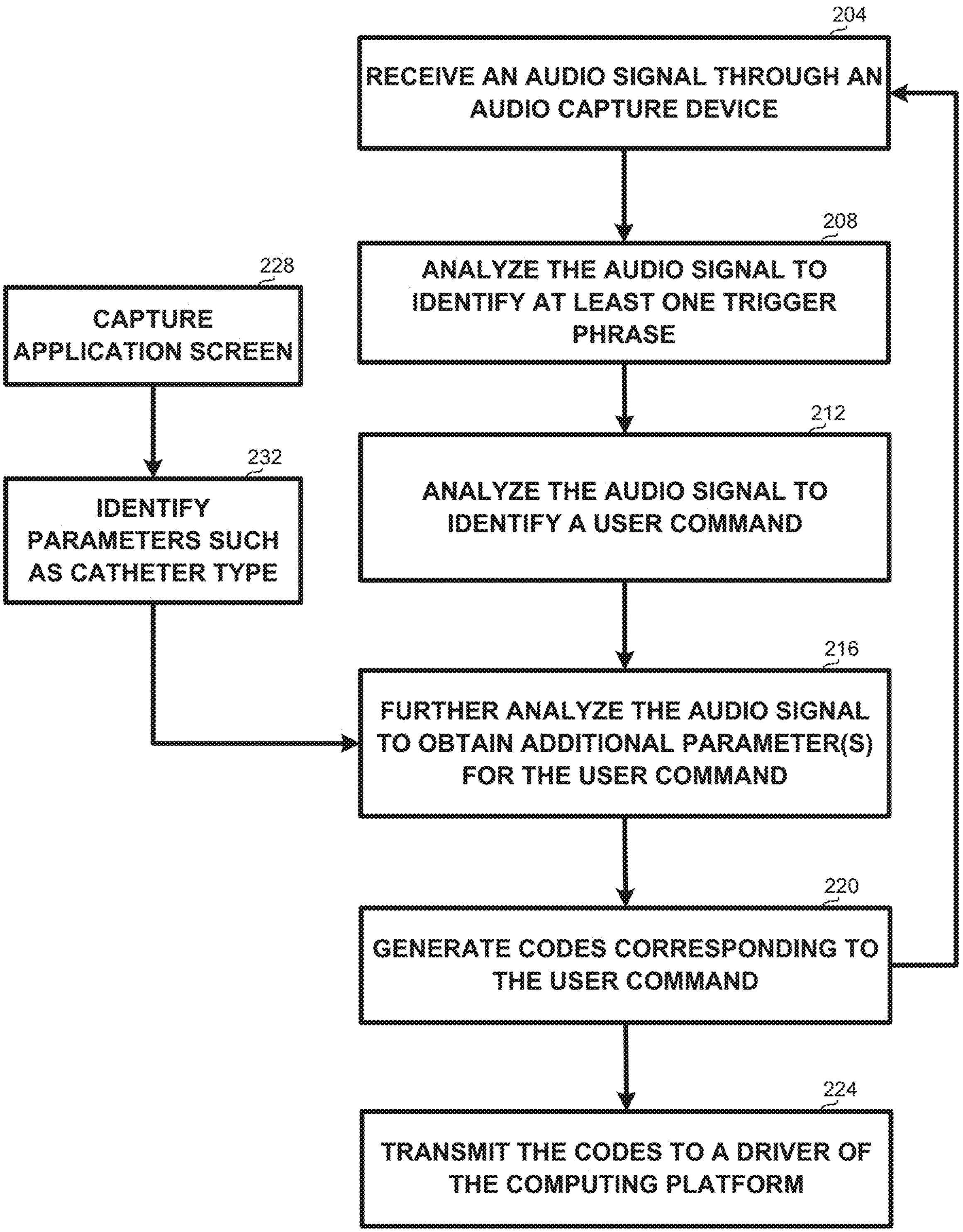
FIG. 2 is a flowchart of steps in a method for operating a voice activated display of an electrophysiology system, in accordance with some exemplary embodiments of the disclosure.

Reference is now made to FIG. 2, showing a flowchart of steps in a method for voice activation of an electrophysiology system, in accordance with some exemplary embodiments of the disclosure.

It is appreciated that the method is performed in addition to all steps related to activating the electrophysiological system, including manipulation of one or more catheters and display of electrograms, ablation sites and other data items.

On step 204, an audio signal may be received through an audio capture device configured for capturing the voice of a user, such as a physician or a CAS. Thus, the audio capture device may output an audio signal comprising the voice of the user throughout the operation.

On step 208 the audio signal may be analyzed to identify at least one predetermined trigger phrase comprising one or more words.

For example, whenever the user wishes to issue a voice command, the user can say a predetermined trigger word or phrase, such as “Carto”, “Carto operate”, “display please”, “start display”, or the like.

Once the speech recognition module identifies the trigger phrase, on step 212 the same module or a different audio analysis module may continue analyzing the audio signal to retrieve a user command from a predetermined set of user commands for which vocal activation is enabled.

The user commands may be identified using a classifier receiving as input the audio signal and outputting an identifier of one of the predetermined user commands for which vocal activation is enabled. The classifier may be trained upon a plurality of audio signals, and a label associating each audio signal with a user command, such that the classifier learns the connections between features of the audio signals and the associated user commands. Then during runtime, the classifier may identify the user command that best matches the audio signal. In some embodiments, the classifier may output for each possible user command a certainty level that the audio signal relates to the user command. Then, the user command having the highest certainty level may be selected and the selected user command may be executed.

In some embodiments, if two or more commands have similar certainty levels, for example certainty levels differing in at most a predetermined threshold, the two or more commands may be displayed textually over the display device, or read aloud to the user using a speaker embedded within workstation 55 or external thereto, such that the user can select either or none of them.

If a user command is recognized, a confirmation sound or audio file may be played by a speaker, while if no user command is recognized, for example if the highest certainty level associated with any of the user commands is below a predetermined threshold, the system may play an audio file indicating that the captured audio is unclear, not associated with a user command, incorrect, or the like, or the user may be asked to repeat or to confirm that a command recognized by the system is correct.

On step 216, the audio signal may be further analyzed for obtaining one or more parameters related to the user command. For example, if the user command indicates that the user wants to see only a certain electrogram, the user has to provide the number of the corresponding electrode. Thus, on step 216, if the audio signal is classified as a user command intended for viewing a specific electrogram, the audio may be further analyzed to retrieve an electrode number. The parameter recognition may also use small vocabulary speech recognition, in which the vocabulary is comprised of words related to possible parameters of the system, such as letters, numbers, or the like. In some embodiments, recognizing the parameter may be performed by a corresponding trained classifier.

On step 220, one or more codes corresponding to the identified user command may be generated. The term code relates to a binary code or signal that may be provided to a driver of the underlying computing platform and is indicative of a user action such as a key press, a mouse event, a pointing device event, or the like.

On step 224, the generated codes may be provided to a driver of the operating system of the computing platform, such as workstation 55. The driver may generate corresponding events and append or insert the events to the event queue. The events may then be handled as any other event on the queue, which is identical to what would have happened with an event generated upon the user hitting a key or manipulating the pointing device.

In some embodiments, the application may also comprise an image capture module or device for capturing an image of the display of the electrophysiology system, and an image analysis module for analyzing the captured image.

Thus, on step 228 the image capture module may capture the display of the electrophysiology system, as may be displayed, for example, on display device 27, and on step 232 the image may be analyzed for obtaining parameters of the electrophysiology system, such as catheter type, number of splines, number of electrodes, or the like, without having to query the electrophysiology system.

In such embodiments, the identified parameters may be utilized during user command identification step 212 to limit the possibilities of what the physician said to commands and parameters relevant to the current way the physician is operating the system. For example, if the physician is using a diagnostic catheter with 20 electrodes, and the voice recognition system is not sure if the physician wants to see the signal from electrode 13 or electrode 30, the voice recognition system can use the knowledge that there are only 20 electrodes to assume that the physician asked to show the signal from electrode 13. Once the options are limited or configured to a predefined list, voice recognition is easier and can be more robust.

In some embodiments, capturing and analyzing the images of the display may be performed one or more times until the required information is obtained at a certainty level exceeding a threshold, and then does not need to be repeated as the operation continues with the same catheter.

Steps 204 and subsequent steps may be performed continuously as the user may issue further user commands, possibly altering previous ones. Thus, the display may keep updating with new data, for example as electrograms are continuously updated with new readings, and the displayed item(s) or their presentation may change if the user issues new user commands.

It is appreciated that the user may also keep providing user commands in any other manner, for example through the user interface or by the CAS.

Figure 3:
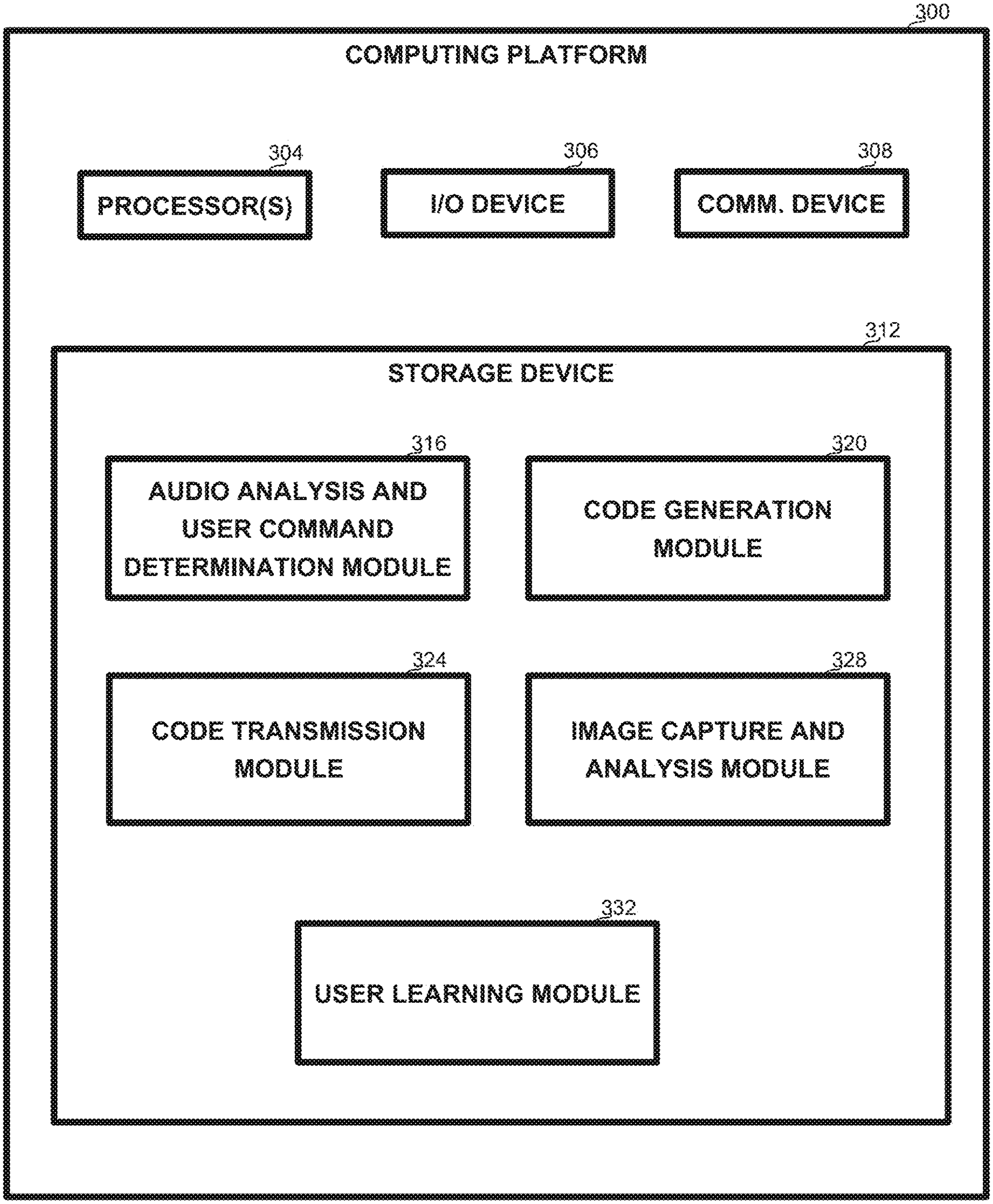
FIG. 3 is a schematic block diagram of a computing platform for voice activated display of an electrophysiology system, in accordance with some exemplary embodiments of the disclosure.

Referring now to FIG. 3, showing a block diagram of a computing platform 300 for operating a voice activated display of an electrophysiology system, in accordance with some exemplary embodiments of the disclosure.

It is appreciated that computing platform 300 may be embedded within workstation 55, but may also be a standalone computing platform, or embedded elsewhere and be in operative communication with workstation 55.

Computing platform 300 may be implemented as one or more computing platforms which may be operatively connected to each other. For example, one or more remote computing platforms, which may be implemented for example on a cloud computer. Other computing platforms may be a part of a computer network of the associated organization. In other embodiments, all the functionality may be provided by one or more computing platforms all being a part of the organization network.

Computing platform 300 may comprise one or more processors 304 located on the same computing platform or not, which may be one or more Central Processing Units (CPU), microprocessors, electronic circuits, Integrated Circuits (IC) or the like. Processor 304 may be configured to provide the required functionality, for example by loading to memory and activating the software modules stored on storage device 312 detailed below.

Computing platform 300 may comprise one or more I/O devices 306, such as a microphone for capturing the user's voice, a speaker for playing audio, a display which may be implemented as part of display 21, 27 or another display, a keyboard, a mouse, a touchscreen, another pointing device, or the like.

Computing platform 300 may comprise a communication device 308 for communicating with other devices or other computing platforms as necessary, for example obtaining information from the catheterization controller indicating locations and electrical measurements, storing data on remote storage devices, obtaining information related to performed ablations, or the like. Communication module 308 may be adapted to interface with any communication channel such as Local Area Network (LAN), Wide Area Network (WAN), cellular network or the like, and use any relevant communication protocol.

Computing platform 300 may comprise a storage device 312, such as a hard disk drive, a Flash disk, a Random Access Memory (RAM), a memory chip, or the like. In some exemplary embodiments, storage device 312 may retain program code operative to cause processor 304 to perform acts associated with any of the modules listed below, or steps of the method of FIG. 2 above. The program code may comprise one or more executable units, such as functions, libraries, standalone programs or the like, adapted to execute instructions as detailed below.

Alternatively or additionally, the provided instructions may be stored on non-transitory tangible computer-readable media, such as magnetic, optical, or electronic memory.

Storage device 312 may comprise one or more audio analysis and user command determination module 316. Audio analysis and user command determination module 316 may comprise small vocabulary recognition module, for recognizing the trigger phrase preceding a user command, and for recognizing specific predetermined user commands. The small vocabulary recognition module may also be useful in recognizing parameters related to one or more user commands, such as electrode identifiers.

Additionally or alternatively, module 316 may comprise large vocabulary recognition module, also referred to as free speech recognition module, for recognizing user within free speech not limited to specific commands vocabulary, and determining the highest matching user command available for vocal activation.

If 316 comprises large module a vocabulary recognition module, the apparatus may also comprise text analysis capabilities for parsing or otherwise analyzing the retrieved speech and recognizing user commands.

Storage device 312 may comprise code generation module 320 for generating one or more codes imitating the codes that would be generated had the user performed the actions required for the same user command.

Storage device 312 may comprise code transmission module 324 for providing the codes to a driver of the underlying operating system, which in turn generates corresponding events and queues them to the event queue, such that they can be handled by the electrophysiology system.

Storage device 312 may comprise image capture and analysis module 328 for capturing the screen of the electrophysiology system or part thereof, and analyzing it. Analysis may include discovering information such as catheter type, number of splines or electrodes, or the like, without having to interface with the electrophysiology system. Obtaining these parameters may help determine parameters of the commands said by the user, for example ruling out displaying electrograms of unavailable electrodes or other impossible combinations.

Storage device 312 may comprise user learning module 332, which may comprise one or more learning modules related to one or more users. For example, user learning module 332 may comprise a voice signature learning module for obtaining a voice signature of the user such that future voice recognition is more efficient and more accurate than before the signature is available. Thus, when the user enrolls with the system, the user may provide a voice sample upon which a voice signature is trained, and when the user identifies with the system, the respective voice signature is retrieved. In alternative embodiments, the relevant voice signature is retrieved based on the user's voice as captured at the beginning of the operation. The user's signature may also be updated based on the newly acquired voice.

It is appreciated that the steps and modules disclosed above are in addition to the software, hardware, firmware or other for operating the catheter, displaying the catheterization process, performing other calculations such as signal analysis and in particular complex fractionated electrogram (CFE) analysis, generating the heart map, or the like. Further details for methods and systems may be found, for example in U.S. Pat. Nos. 8,676,305, 9,629,567, incorporated herein by reference in their entirety for any purpose.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture instructions, machine instructions, machine dependent instructions, microcode, firmware instructions, state-setting data, or either source code or object code written in any combination of one or more programming languages, programming languages such as Java, C, C++, Python, or others. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

EXAMPLES

Example 1

A method comprising: within an electrophysiology system executed by a computing platform and comprising a voice capture device: receiving an audio signal captured by an audio capture device; analyzing the audio signal to retrieve at least one trigger phrase; in response to identifying the trigger phrase, further analyzing the audio signal to identify one or more words associated with a user command; generating at least one code corresponding to the user command; and transmitting the at least one code to a driver of the computing platform, thereby causing execution of the user command by the electrophysiology system.

Example 2

The method according to example 1, further comprising analyzing the audio signal to identify a parameter related to the user command.

Example 3

The method according to example 1, further comprising: obtaining a screen capture of a display of the electrophysiology system; analyzing the screen capture to obtain a parameter of the electrophysiology system; and utilizing the parameter for identifying the user command or a parameter thereof.

Example 4

The method according to example 1, wherein the user command is selected from a predetermined collection of user commands.

Example 5

The method according to example 4, wherein the predetermined collection of user commands is a subset of a larger set of user commands available in the electrophysiology system.

Example 6

The method according to example 5, wherein the predetermined collection of user commands comprises at most 25% of the larger set of user commands.

Example 7

The method according to example 5, wherein the predetermined collection of user commands comprises at most 10% of the larger set of user commands.

Example 8

A computerized apparatus having a processor coupled with a memory unit, the processor being adapted to perform the steps of: receiving an audio signal captured by an audio capture device; analyzing the audio signal to retrieve at least one trigger phrase; in response to identifying the trigger phrase, further analyzing the audio signal to identify one or more words associated with a user command; generating at least one code corresponding to the user command; and transmitting the at least one code to a driver of the computing platform, thereby causing execution of the user command by the electrophysiology system.

Example 9

The apparatus according to example 8, wherein the audio capture device is a head mounted microphone.

Example 10

The apparatus according to example 8, wherein the processor is further adapted to analyze the audio signal to identify a parameter related to the user command.

Example 11

The apparatus according to example 8, wherein the processor is further adapted to: obtain a screen capture of a display of the electrophysiology system; analyze the screen parameter of capture to obtain a the electrophysiology system; and utilize the parameter for identifying the user command or a parameter thereof.

Example 12

The apparatus according to example 8, wherein the user command is selected from a predetermined collection of user commands.

Example 13

The apparatus according to example 12, wherein the predetermined collection of user commands is a subset of a larger set of user commands available in the electrophysiology system.

Example 14

The apparatus according to example 13, wherein the predetermined collection of user commands comprises at most 25% of the larger set of user commands.

Example 15

The apparatus according to example 13, wherein the predetermined collection of user commands comprises at most 10% of the larger set of user commands.

Example 16

A computer program product comprising a non-transitory computer readable storage medium retaining program instructions configured to cause a processor to perform actions, which program instructions implement: receiving an audio signal captured by an audio capture device; analyzing the audio signal to retrieve at least one trigger phrase; in response to identifying the trigger phrase, further analyzing the audio signal to identify one or more words associated with a user command; generating at least one code corresponding to the user command; and transmitting the at least one code to a driver of the computing platform, thereby causing execution of the user command by an electrophysiology system.

Although the examples described herein mainly address cardiac diagnostic applications, the methods and systems described herein can also be used in other medical applications.

It will be appreciated that the examples described above are cited by way of example, and that the present disclosure is not limited to what has been particularly shown and described hereinabove. Rather, the scope of the present disclosure includes both combinations and subcombinations of the various features described hereinabove, as well as variations and modifications thereof which would occur to persons skilled in the art upon reading the foregoing description and which are not disclosed in the prior art.

The invention claimed is:

1. A method comprising:

within an electrophysiology system executed by a computing platform and comprising a voice capture device:

obtaining a screen capture of a display of the electrophysiology system;

analyzing the screen capture to obtain a parameter of the electrophysiology system;

receiving an audio signal captured by an audio capture device;

analyzing the audio signal to retrieve at least one trigger phrase;

in response to identifying the trigger phrase, further analyzing the audio signal to identify a user command based at least in part on the parameter of the electrophysiology system;

generating at least one code corresponding to the user command; and transmitting the at least one code to a driver of the computing platform, thereby causing execution of the user command by the electrophysiology system.

2. The method of claim 1, further comprising analyzing the audio signal to identify a command parameter related to the user command.

3. The method of claim 1, wherein the user command is selected from a predetermined collection of user commands.

4. The method of claim 3, wherein the predetermined collection of user commands is a subset of a larger set of user commands available in the electrophysiology system.

5. The method of claim 4, wherein the predetermined collection of user commands comprises at most 25% of the larger set of user commands.

6. The method of claim 4, wherein the predetermined collection of user commands comprises at most 10% of the larger set of user commands.

7. A computerized apparatus having a processor coupled with a memory unit, the processor being adapted to perform the steps of:

obtaining a screen capture of a display of an electrophysiology system;

analyzing the screen capture to obtain a parameter of the electrophysiology system;

receiving an audio signal captured by an audio capture device;

analyzing the audio signal to retrieve at least one trigger phrase;

in response to identifying the trigger phrase, further analyzing the audio signal to identify a user command based at least in part on the parameter of the electrophysiology system;

generating at least one code corresponding to the user command; and transmitting the at least one code to a driver of the electrophysiology system, thereby causing execution of the user command by the electrophysiology system.

8. The apparatus of claim 7, wherein the audio capture device is a head mounted microphone.

9. The apparatus of claim 7, wherein the processor is further adapted to analyze the audio signal to identify a command parameter related to the user command.

10. The apparatus of claim 7, wherein the user command is selected from a predetermined collection of user commands.

11. The apparatus of claim 10, wherein the predetermined collection of user commands is a subset of a larger set of user commands available in the electrophysiology system.

12. The apparatus of claim 11, wherein the predetermined collection of user commands comprises at most 25% of the larger set of user commands.

13. The apparatus of claim 11, wherein the predetermined collection of user commands comprises at most 10% of the larger set of user commands.

14. A computer program product comprising a non-transitory computer readable storage medium retaining program instructions configured to cause a processor to perform actions, which program instructions implement:

obtaining a screen capture of a display of an electrophysiology system;

analyzing the screen capture to obtain a parameter of the electrophysiology system;

receiving an audio signal captured by an audio capture device;

analyzing the audio signal to retrieve at least one trigger phrase;

in response to identifying the trigger phrase, further analyzing the audio signal to identify a user command based at least in part on the parameter of the electrophysiology system;

generating at least one code corresponding to the user command; and transmitting the at least one code to a driver of the electrophysiology system, thereby causing execution of the user command by an electrophysiology system.

15. The computer program product of claim 14, wherein the program instructions further implement:

analyzing the audio signal to identify a command parameter related to the user command.

16. The computer program product of claim 14, wherein the user command is selected from a predetermined collection of user commands.

17. The computer program product of claim 16, wherein the predetermined collection of user commands is a subset of a larger set of user commands available in the electrophysiology system.

18. The computer program product of claim 17, wherein the predetermined collection of user commands comprises at most 25% of the larger set of user commands.

19. The computer program product of claim 17, wherein the predetermined collection of user commands comprises at most 10% of the larger set of user commands.

* * * * *